(12) United States Patent
Noorchashm et al.

(10) Patent No.: US 10,905,715 B2
(45) Date of Patent: Feb. 2, 2021

(54) AUTOLOGOUS IMPLANTATION OF CHIMERIC MURINE-HUMAN TUMORS, GENERATED IN PDX MICE, FOR ATIVATION OF AN ANTI-TUMOR IMMUNE RESPONSE IN THE DONOR PATIENT

(71) Applicants: Hooman Noorchashm, Yardley, PA (US); Amy J. Reed, Yardley, PA (US)

(72) Inventors: Hooman Noorchashm, Yardley, PA (US); Amy J. Reed, Yardley, PA (US)

( * ) Notice: Subject to any disclaimer, the term of this patent is extended or adjusted under 35 U.S.C. 154(b) by 730 days.

(21) Appl. No.: 15/452,165

(22) Filed: Mar. 7, 2017

(65) Prior Publication Data

US 2017/0252371 A1 Sep. 7, 2017

Related U.S. Application Data

(60) Provisional application No. 62/304,894, filed on Mar. 7, 2016.

(51) Int. Cl.
*A61K 35/13* (2015.01)
*C12N 5/00* (2006.01)

(52) U.S. Cl.
CPC ............... *A61K 35/13* (2013.01); *C12N 5/00* (2013.01)

(58) Field of Classification Search
None
See application file for complete search history.

(56) References Cited

PUBLICATIONS

Stebbing, Justin, et al. "Patient-derived xenografts for individualized care in advanced sarcoma." Cancer 120.13 (2014): 2006-2015. (Year: 2014).*

* cited by examiner

*Primary Examiner* — Robert J Yamasaki
(74) *Attorney, Agent, or Firm* — Ladas & Parry LLP (57) ABSTRACT

Here, we present a specific and novel method for treating cancer by eliciting an anti-tumor immune response in cancer patients. Specifically, this technique involves subcutaneous "auto-im-transplantation" of chimeric murine-human tumors, created in PDX mice, back to the original donor patients. This is an approach to personalized cancer therapy, which does not require identification of specific tumor associated antigens. Based on the fundamental principles of immunology, we anticipate that the autoimplanted PDX tumor will stimulate an intense immune response in the original donor patient—including activation of "xenoreactive" lymphocytes and, in turn, a "bystander" activation of anti-tumor immune response lymphocytes, which we anticipate that a response generated in this manner will become systemic and target other similar malignant cells in the patient. Once such an immune response is activated, it is expected to promote overall regression, or cure, of the malignant state by killing in cancerous cells in the donor cancer patient.

21 Claims, 5 Drawing Sheets
(5 of 5 Drawing Sheet(s) Filed in Color)

AUTOLOGOUS IMPLANTATION OF CHIMERIC MURINE-HUMAN TUMORS, GENERATED IN PDX MICE, FOR ATIVATION OF AN ANTI-TUMOR IMMUNE RESPONSE IN THE DONOR PATIENT

RELATED APPLICATION

The present application claims priority from Application 62/304,894 filed on Mar. 7, 2016, the contents of which are incorporated herein in their entirety.

BACKGROUND

Field of the Invention

This invention is in the field of cancer treatment and cure via immunotherapy. More particularly, the present invention describes a novel approach to activating an anti-tumor immune response in patients with cancer.

Description of the Related Art

A major barrier to cure of cancer in mans is the inability of the immune system to effectively activate an anti-tumor immune response—this phenomenon is known as immunological tolerance. Over the past several decades, major efforts have been dedicated to the development of tumor vaccines, tumor specific antibodies and T-cells, as well as, other means of triggering the immune system to break tolerance and to kill cancerous tissues. These includes autologous cellular vaccines with synthetic and natural adjuvants, peptide and whole antigen vaccines, genetically engineered vaccines, monoclonal antibodies specific for tumor antigen(s), in vivo stimulation of tumor reactive T-cells with auto-transfusion, genetically engineered tumor specific T-cells (i.e., CAR T-cells) with auto-infusion, among other techniques.

Unfortunately, however, in the vast majority of cases the cancer patient's immune system remains tolerant to the tumor and the patients eventually succumb to their disease. Recently a range of targets of immunotherapy have been developed—these include PD-1 and CTLA-4. When these targets are blocked, T-cell activation thresholds are lowered in the case of certain tumors in which T-cell targeting has already occurred—notably these agents have met dramatic success in the case of melanomas. Effective priming of an anti-tumor T-cell response seems to be the limiting step in the generation curative tumor immunity.

SUMMARY

The present invention is a novel, and hitherto untested, method of priming an anti-tumor immune response in humans or other animals by implanting autologous chimeric murine-human tumors back into a donor patient. In this way this approach is an example of personalized immunotherapy.

Briefly, cancerous tissue from a specific patient is transplanted into unique immunodeficient strains of mice, which are genetically capable of accepting and growing both allogeneic and xenogeneic tissues. The human donor tissue heals in and, typically, functions in these recipient mouse as it does in the donor. These tumor-bearing mice are generally known as "Patient Derived Xenograft" (PDX) mice and have been developed and commercialized extensively for the study of cancer biology, and other biomedical disciplines, over the past decade.

In the case of xenogeneic cancers transplanted from patients into mice, the tumors typically grow and thrive. Over the course of several weeks to months as the tumor establishes itself in the recipient mice, it becomes "chimeric". That is, the tumor is a "chimera" made of the human cancer and murine cellular, stromal and matrix elements.

The central idea presented in this application is that harvesting the well-established PDX tumor from the mice and implanting these "chimeric" tumors back into the original donor patient will stimulate a robust anti-tumor immune response.

The present invention differs from other immunotherapeutic approaches, such as CAR T Cell therapy where T-cells from a patient are engineered to express a tumor-specific chimeric antigen receptor.

The present invention is similar to autologous tumor vaccines in that it relies on developing an immunogenic preparations that includes the patient's own tumor. This preparation requires generation of a human-mouse chimeric tumor in a PDX mouse, which is then implanted back into the donor patient. Based on its chimeric nature, this reimplanted tumor is targeted by the patient's immune system since it is recognized as being "non-self", or foreign, because the tumor is "decorated" by xenogeneic tissues and antigens derived from the recipient mouse. In the process of immunological targeting it is expected that lymphocytes specific for tumor antigens will participate in the ongoing inflammation and become primed.

The invention utilizes the phenomenon of "bystander lymphocyte activation". This is a well studied basic immunological phenomenon in which immune tolerance can be broken using linked immunity—that is expression of foreign antigens in organs and tissues can precipitate a loss of tolerance to the tissue's "self antigens" when the foreign antigen is targeted. It is these basic processes the autoimplantation of PDX tumors relies on to approaching "breaking immunological tolerance" to tumor antigens in the cancer patient. This approach is a novel personalized approach to immunotherapy, which could target a broad array of the patient's tumor antigens without the need to knowing the precise identity of these antigens.

Mechanistically, in a pro-inflammatory milieu created by the xenogeneic mouse tissue, lymphocytes that are ordinarily insufficiently activated (i.e., the tumor-reactive or self-reactive ones) will be activated based on the pro-inflammatory milieu created by the xenoimmune response.

It is important to note that this approach "personalizes" cancer immunotherapy by using a "chimeric" version of the patient's own tumor to instigate an immune response.

Accordingly the present invention provides a method for treating a human or other animal patient (e.g., dogs, cats, etc.) having cancerous tumors which comprises:
1) Removing at least part of the tumor from the patient;
2) Implanting the tumor in an immuno deficient recipient host animal;
3) Allowing the tumor to grow in the recipient host animal to form a chimeric tumor;
4) Removing at least part of the chimeric tumor from the host animal;
5) Processing the chimeric tumor to attenuate or kill live cancer cells in said removed part of the chimeric tumor; and
6) Auto-implanting all or part of said removed part of said chimeric tumor into the original tumor donor patient.

BRIEF DESCRIPTION OF THE DRAWINGS

The file of this patent contains at least one drawing or photograph executed in color. Copies of this patent color drawing(s) or photograph(s) will be provided by the Patent and Trademark Office upon request and payment of necessary fee.

DETAILED DESCRIPTION

The method of the present invention is suitable for treating any malignant solid tumors—irrespective of metastatic stage—including, but not limited to, Sarcomas, Adenocarcinomas, Melanomas, which can be transplanted and develop in recipient host animals such as NSG mice.

Resected or biopsied tumor samples from the patient are used to implanted into an immunodeficient host animal. Such animals are desirably T-cell, B-cell and NK-cell deficient and can include immunodeficient mice such as the NSG™ strain mouse, the NOD/scid, the nude mouse or an NIH III nude mouse. Other useful hosts may include immunodeficient rats such as immunodeficient pigs capable of growing patient derived xenografts.

Typically the blocks of tumor inserted subcutaneously into the recipient animal. These donor tumors blocks are to be of a minimum size to permit engraftment and will typically be 1-3 mm$^3$.

The tumor blocks implanted in the host animal is then allowed to grow for three to six months before removal for implantation into the patient. Typically the tumors can grow to a size of 2-3 cm$^3$ without compromising the recipient mouse's life The chimeric nature of the growing tumors may be confirmed by using immunohistochemical analysis with monoclonal antibodies specific for the host animal markers such as mouse markers CD31, CD34, and CD45. That is, the PDX tumor will be the cancerous human tissue laced with mouse-derived cells from the recipient host.

It may be useful to seed, by injection, the implanted tumor with an immunostimulatory immune agonist, for example a TLR agonist such as CpG7909. Alternatively, immunostimulatory transgenes, such as IFN-gamma or IL-2, can be bred into the recipient host in order to ensure the presence of such immunostimulatory elements when the PDX is implanted back into the original donor patient.

Once the tumor has grown to a suitable size, all or part of it is removed from the host animal and treated to destroy or attenuate live cancer cells—for example this can be done by irradiation, cryo-killing or a combination thereof. When irradiation is used, this will be effected by use of gamma radiation, for example using doses of 3,000 to 5,000 rads. Cryo-killing can be effected, for example by subjecting the PDX tumor to multiple freeze-thaw cycles to −80° C. or using liquid nitrogen.

The chimeric PDX tumor is then ready for implantation into the patient from whom the initial tumor was resected or biopsied. Such "auto-implantation" is typically performed into a subcutaneous pocket in the arms, thighs or flank of the patient. Such pockets are formed by incisions of 1.5-3 cm down to the layer of subcutaneous fat. The processed chimeric tumor is minced using a scalpel and implanted at a size of from 1-5 cm$^3$. Mincing the tumor material prior to autoimplantation permits achievement of greater surface area of contact with the patient's own tissue to generate the desired anti-tumor inflammatory response in the patient.

As the goal of this autologous implantation of the PDX tumor is to break tolerance to tumor antigens, repeated treatments may be necessary to reach an inflection point where the anti-tumor immune response has been sufficiently activated to autonomously target and destroy indigenous tumors in the donor patient (i.e., immune tolerance has been broken). The treatment may, thus, be repeated with periods of from two weeks to 3-4 months between successive autoimplantations until evidence of tumor destruction emerges.

In some cases, it may be desirable to combine the treatment of the present invention with other immunotherapeutic regimens. Specifically combination therapy with the available Checkpoint Inhibitor agents many render the immune response more effective. Alternatively, there is substantial evidence that certain systemic chemotherapeutic regimens may potentiate immune responses—these could include metronomic cyclophosphamide or other transient lympho-depleting agents and approached.

Additionally, following PDX autoimplantation, select indigenous tumors in the patient can be injected with immunostimualtory agents—such as TLR agonists, or other innate immune system stimulators—to attract lymphocytes to the patient's tumors.

Adjunctive therapies that could render the subject patients' other indigenous metastatic lesions susceptible to immunological attack—these include but are not limited to direct intra-tumoral injection with microbial derivatives, synthetic immunogenic biologics (such as TLR agonists, cytokines, etc.), cryoablation, and stereotactic radiation.

More specifically, the present invention involves the generation of mice known as "Patient Derived Xenograft" (i.e., PDX) mice. Cancerous tissue resected by a surgeon from a specific patient can be transplanted into various different immunodeficient strains of mice. The most powerful and effective strain of mice used to create PDX is known as the NSG™ strain. Other related strains, such as NOD/scid, nude, etc. can also be used as recipients of human tissues. These NSG™ recipient mice were genetically engineered at the Jackson Laboratory (Bar Harbor, Me.) to accept both allogeneic and xenogeneic tissues—and are the most commonly used strain for generation of PDX mice in the scientific literature. The donor tissue heals well in NSG™ mice and, typically, functions as it does in the donor.

The critical feature of the transplanted tissue in the recipient mice, for the present patent application, is that they become "chimeric" as they heal in and grow in their murine host. That is, the donor tissue is "fed" by recipient derived angiogenesis. It is "infiltrated" by recipient mouse-derived cells, and it becomes embedded in a biomatrix made up of the murine cellular and stromal elements. NSG™ mice with implanted human tumors are then referred to as "PDX" mice—or "Avatar" mice.

When xenogeneic cancers are transplanted from humans into the NSG mice, the tumors typically grow and thrive. Over the course of several weeks to months as the tumor establishes itself and grows in the recipient mice, it becomes "chimeric". That is, the tumor is a "chimera" made of the human cancer and murine cellular and matrix elements.

Figure 1:
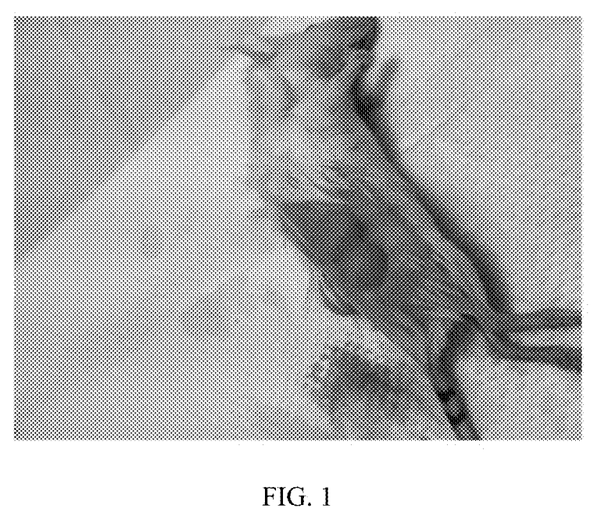
FIG. 1 shows a human cancer, known as a Leiomyosarcoma, implanted and growing in an NSG recipient.
Figure 2:
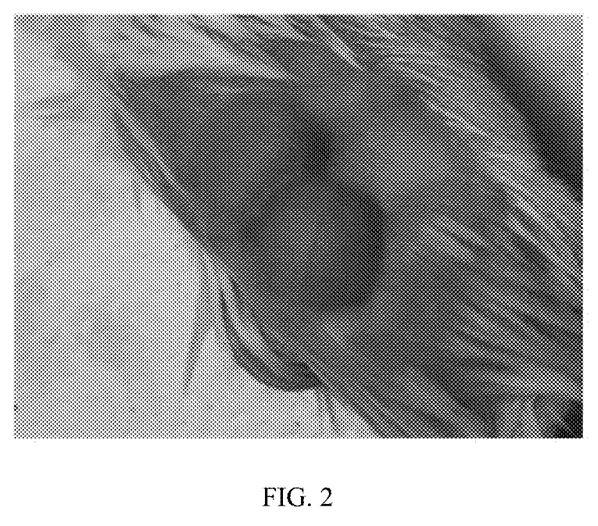
FIG. 2 and FIG. 3 are enlarged pictures showing the growth of the tumor.
Figure 3:
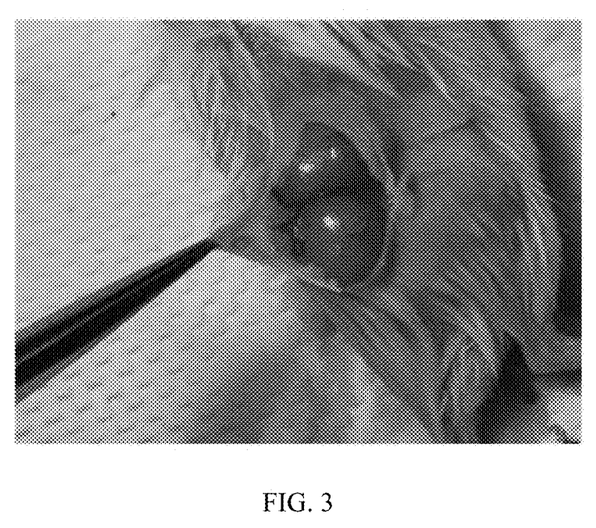
Figure 4:
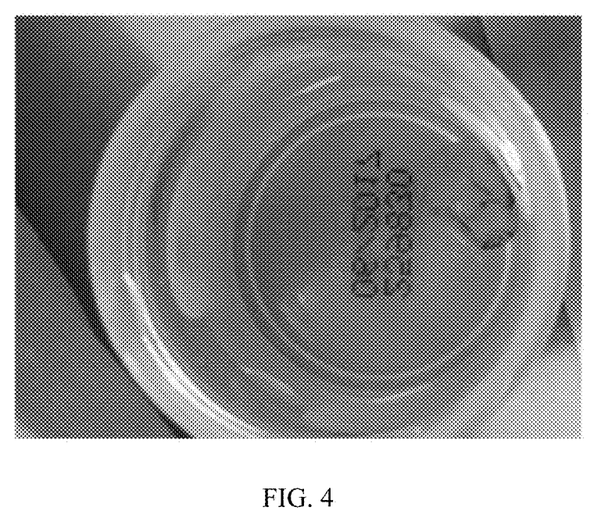
FIG. 4 A gross picture of a PDX tumor removed from a mouse recipient
Figure 5:
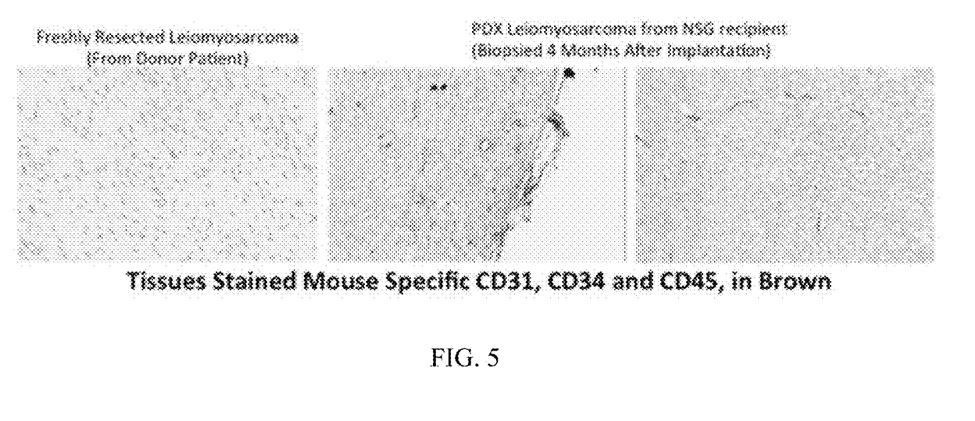
FIG. 5 shows leimycosarcoma tissue samples freshly removed from a patient and also after four months growth in NSG mouse.

FIGS. 1-4 show an example of an aggressive human cancer, known as a leiomyosarcoma, implanted and growing in an NSG recipient:

The following is immunohistological analysis of the above biopsied PDX tumor in comparison to the donor cancer freshly resected from the patient. The tissue are stained using mouse specific markers (i.e., CD31, 34, and 45) in Brown. Most importantly, no brown staining is detected in the tumor resected from the patients. But there are abundant mouse derived tissues detected in the PDX tumor derived from the patient. This finding confirms that PDX tumors are murine-human chimeras, as expected.

Most importantly, in the present application, we rely on the murine-human "chimerism" established in the PDX tumors by virtue of the tumor being nourished and growing in the mouse recipient.

It is a fundamental principle of cellular immunology that "chimeric" tissues are efficiently rejected by a donor-type immune system. It is, in fact, a logical prediction that the xenogeneic murine components of the chimeric tumors from the PDX mice will be rapidly targeted by the human immune system for destruction. We anticipate that this immunological targeting and rejection of PDX chimeric tumors by the donor patient will recruit and trigger a powerful tumor specific "bystander immune response"—one, which will hopefully become systemic after multiple rounds of PDX implantation.

The following is a step-by-step procedure that may be used to implement the present invention:

1) Surgical resection of live tumor from a cancer patient by a surgical oncologist or general surgeon
2) Temporary storage of isolated tumor in under suitable conditions, for example cold saline with antibiotics and transport to the mouse transplant facility.
3) Subcutaneous transplantation of parts of the isolated tumor into immunodeficient mice that are capable of accepting and nurturing human tissues, for example NSG or NOD/scid nude mice. Other possible animal hosts include NOD/SCID/$\gamma c^{null}$ and Rag2$^{null}\gamma c^{null}$ mice. Conveniently 2-3 mm fragments of tumor are inserted into four quadrants in the torso of the animal to generate 5-10 "PDX" mice per patient.
4) The tumor fragments are allowed to grow in the host animal, for example for 2-3 months to confirm tumor viability and growth in the "PDX" mice. Biopsy of one tumor quadrant for histology to confirm viable tumor growth and confirmation of chimerism.
5) Harvest 1-5 cm$^3$ blocks of the "chimeric" tumor from 3-5 of the PDX mice.
6) Patient allergy testing (i.e., skin allergen testing and measurement of serum IgE titers of anti-mouse extract) in the donor patient to determine whether an allergic response to mouse antigen(s) is present. If an allergic skin test is detected, a desensitization protocol is undertaken, as is the standard of care offered by Allergy and Immunology specialists.
7) Cryokilling of the tumor, for example repeat freeze-thaw cycles in sterile saline at −80° C. or using liquid nitrogen—or irradiation to inactivate tumor cells for example using 3300-4000 rads gamma radiation.
8) "Autotransplantation" of the PDX tumor back into the original human tumor donor. The PDX tumor will be minced up prior to autoimplantation and can be implanted live, or inactivated as described in step 7. The "auto-implantation" technique will involve creation of a subcutaneous pocket under sterile conditions, in an operating room using light sedation or general anesthesia. The pocket will be created in the forearms, flank or thighs—and the harvested PDX tumor will be implanted into this space. The subcutaneous tissue and overlying skin will be closed in 2-3 layers using absorbable suture material.
9) As an important corollary, the cancer patient being autoimplanted can be treated with clinically approved systemic immune adjuvant agents or with checkpoint inhibitors (e.g., Opdivo, Yervoy, etc.) while awaiting the growth of their PDX tumor. This maneuver could enhance the probability of a successful anti-tumor immune response following implantation of the PDX tumor.

When an immune response is directed at the PDX tumor, it is possible that lymphocytes specific for, both, tumor mutant antigens and the normal self-antigens expressed by the tumor will be activated. Therefore, as with any immunotherapy strategy directed at tumors, the possibility of autoimmunity lurks. It is essential to highlight, however, that the possibility of autoimmunity is a function of the tumor being more "self" than it is "non-self"—and that this side-effect lurks in most immunotherapeutic approaches. For example, the novel immunotherapeutic drugs that have recently made a wave are the Checkpoint Inhibitors (e.g., Keytruda, Yervoy, Opdivo, etc). These agents all have as side-effects autoimmune reactions such as pneumonitis, hepatitis, colitis—that is, instances where the immune system is unleashed in normal healthy tissue. However, an object of the present invention is to "break tolerance" to a cancer that is more self than it is non-self and so any autoimmune response should be manageable. In the index patient whose treatment is described in the Example, despite a robust inflammatory response to the autoimplanted PDX tumor, no clinical evidence of autoimmunity from the implants emerged. Nevertheless, patients being treated by the method of the present invention should be carefully monitored for any signs of autoimmunity.

The approach relies on the well-establish immune response mounted against xenograft tissues (in this case derived from a mouse) but applies this in a novel way to achieve tumor reactive T-cells and lymphocytes will undergo "bystander activation" of tumor reactive T-cells and lymphocytes in a pro-inflammatory milieu creation by the immune reaction to xeno-antigens.

Example

Treatments Prior to Treatment According to the Invention

The patient, was a 42 year old female with a diagnosis of high grade metastatic uterine Leiomyosarcoma (uLMS). This cancer was initially diagnosed following a routine minimally invasive hysterectomy for presumed benign fibroid disease Unfortunately, this uLMS was partially morcellated leading to abdominal-pelvic dissemination of the cancer. The pathology on the primary tumor demonstrated a high grade Leiomyosarcoma based on its high mitotic rate and question of lymphovascular invasion.

Prior to treatment in accordance with the present invention, the patient underwent a cytoreduction/HIPEC operation (i.e., the Sugarbaker" procedure to remove and kill the morcellated bits of uLMS from her abdominal cavity. Following recovery from this operation, the patient underwent systemic chemotherapy She tolerated these treatments well and remained with "No Evidence of Disease" for just over a year After which she had multiple metastases to her Lumbar and thoracic spine, right and left lungs, left medial thigh, left acetabulum, and pelvis. With the exception of the left lung lesion, measuring 1.1 cm on her last Chest CT scan, and the left pelvic mass, measuring 2-3 cm on last MRI, at the time of the first treatment according to the present invention all other lesions were resected or stereotactically irradiated.

Twenty-six months after the initial diagnosis, after multiple recurrences every 2-3 months the patient was started on an off-label regimen of Nivolumab and Ipilimumab. These treatments are ongoing at two 2-week intervals—alternating Nivolumab (3 mg/kg) with combined Nivolumab/Ipilimumab. She has tolerated these treatments. The patient received two doses of an experimental "homemade" tumor vaccine immediately following her second and third combined doses of Nivolumab/Ipilimumab. This vaccine consisted of $5-7 \times 10^6$ cryo-killed and irradiated autologous tumor cells isolated from one of her resected tumors. This cellular prep was emulsified with Montanide and the TLR9 agonist, CpG7909, as an adjuvant. She tolerated these priming vaccine doses well, with no systemic response and minimal erythema at the injection site in her right lateral thigh.

Treatment According to the Invention

A month prior to the start of the treatment with Nivolumab and Ipilimumab the metastatic lesion resected from the patient's right upper lung lobe was used to create "Patient Derived Xeongraft" (PDX) mice using the NSG mouse strain, distributed by Jackson Laboratory in Bar Harbor, Me. These mice were transplanted subcutaneously using 1 mm$^3$ blocks of the tumor. Since then the transplanted tumors have grown substantially resulting in tumors measuring 2-3 cm$^3$ in dimension in the PDX mice. Using immunohistochemical analysis with monoclonal antibodies specific for the mouse markers CD31, CD34, and CD45, it was demonstrated that the tumors growing in the PDX mice are chimeric. That is, the human tumor tissue is laced with mouse-derived cells from the NSG recipient. Various studies have also demonstrated that PDX tumors are, indeed, chimeric for mouse cells. It is highly likely that PDX tumors are chimeric for a vast array of mouse-derived antigens, stromal elements and cells.

Given the aggressive tempo of metastatic disease development in the patient over the previous year and after careful risk benefit analysis and detailed discussions, the patient decided to proceed with an autoimplantation following administration of her fourth combined dose of Nivolumab/Ipilimumab. Twenty-nine months after the initial diagnosis, the patient had undergone skin allergy testing by an allergist physician the week prior to her first implantation procedure—this ruled out an overt allergic response to mouse allergens, thereby indicating the relatively low risk of a hypersensitivity reaction.

The first chimeric tumor autoimplant was performed uneventfully twenty nine months after initial diagnosis.

The day prior to the implantation, a 2 cm$^3$ PDX tumor was harvested form one of the PDX mice, labelled AJR-S1 and cut into three equal sized. One piece was fixed in formalin for later histological analysis. Two pieces were frozen in sterile saline with ciproflaxin at −80° C. to achieve cryokilling of the tumor. On the same day, the left tumor in a second PDX mouse labelled AJR-S2 was injected with 1 mg of CpG7909 in 100 µl of sterile normal saline to achieve recruitment and activation of TLR9+innate cells into the tumor and maximize implant immunogenicity prior to harvest.

On the day of the implantation it was noted that the CpG injected left PDX tumor in AJR-S2 was cyanotic and slightly enlarged. This was likely related to intra-tumor bleeding from a traumatic injection or related to a reaction to the TLR-9 agonist. Both the infected (left) and uninjected (right) tumors were harvested from AJR-S2. Each was cut into three equal portions. One portion of each was fixed in formalin for later histological analysis.

The tumor samples obtained from AJR-S1 and AJR-S2 PDX mice were packaged in 50 cc conical tubes in sterile saline with ciproflaxin, packaged in multiple bags and irradiated using 3300 rads of gamma irradiation to inactivate the tumor cells.

Prior to implantation of cells from the two mice, the patient commenced a 10 day course of Augmentin. Immediately prior to implantation, the patient took Benadryl, Zyrtec, Percocet and Ibuprofen.

Following the patient having given her informed consent about the procedure to be followed, the patient positioned herself in a partial left lateral decubitus position and after cleansing with chlorohexidine and betadine and effecting local analgesia using 35 cc of standard lidocaine and epinephrine a one inch incision was made on her right lateral thigh down to the subcutaneous fat and a subcutaneous pocket was formed following a natural plane in the fat. Two pieces of the tumor prepared as noted above were then placed in the subcutaneous pocket. After fifteen minutes a further three pieces of tumor were placed in the pocket and fifteen minutes after that the incision was closed.

The patient experienced no severe systemic symptoms. A local inflammatory response was visible and palpable starting day 4 post implantation and lasted for 21 days with a peak between days 7-14. This inflammatory response coincided with systemic symptoms including low a grade temperature and some mild myalgia and arthralgia between days 7 and 14, which resolved without intervention. The incision from the first autoimplantation into the right thigh healed well with several nodules palpable inferior to it. These were likely to be the re-implanted tumors.

The Second Chimeric Tumor Autoimplant

Thirty three days after performing the first tumor autoimplant, the patient received her fifth dose of Nivolumab/Ipilimumab (Opdivo and Yervoy), both at 3 mg/kg. She tolerated these well and it was decided to perform a repeat autoimplantation of the chimeric PDX tumor as a booster the following day using a 3 cm$^3$ PDX tumor was harvested from one of the PDX mice, labeled AJR-S4. This tumor was cut into 8 equal sized slices. A sample was fixed in formalin, labeled AJR-S4, for later histological analysis. The remaining pieces were frozen in sterile Saline with Levofloxacin at −80 degrees Celsius to achieve cryo-killing of the tumor.

The following day, two PDX tumors labeled AJR-S5 were harvested in saline with Ciprofloxacin from another mouse. The tumors were sliced in nine pieces. A sample of AJR-S5 was fixed in formalin for later histological analysis.

The MR-S4 and MR-S5 PDX tumors were packaged in 50 cc conical tubes in sterile saline with antibiotics, packaged in multiple bags and irradiated using 4000 rads of gamma radiation to inactivate the tumor cells.

The second autoimplantation used implants of the irradiated PDX tumors, AJR-S4 and AJR-S5.

Prior to the procedure, the patient started a prophylactic course of Augmentin, which she continued until POD 3. She also treated herself, prophylactically, with Benadryl, Zyrtec, Percocet and Ibuprofen immediately prior to autoimplantation. Pre-operative laboratory studies the day before had revealed no abnormalities in the patient's CBC, CMP and Coagulation parameters. She did demonstrate an Eosinophilia, likely a side effect of her Yervoy therapy.

Following the patient having given her informed consent about the procedure to be followed, she positioned herself in a partial right lateral decubitus position, with left side up and after cleansing with chlorohexidine and betadine and effecting local analgesia using 35 cc of standard lidocaine and epinephine a one inch incision was made on her left lateral thigh down to the subcutaneous fat and a subcutaneous pocket was formed following a natural plane in the fat.

In contrast to the first autoimplant, which involved the use of larger tumor pieces, this booster implant involved the use of two 2-3 cm$^3$ PDX tumors (i.e., AJR-S4 and AJR-S5), which were both minced up into much smaller pieces. This strategy was elected to maximize the surface area of contact for an immune response to form. The PDX tumor pieces were minced up into small pieces under sterile condition and placed in a sterile tray containing saline with ciprofloxacin on the sterile field.

The first several pieces of PDX tumor were then into the subcutaneous pocket and delivered to the base of the pocket. After approximately 10 additional minutes additional PDX tissue was placed in the pocket to ensure that the patient was not developing a hypersensitivity reaction. She remained stable and was communicating throughout the process. After a further ten minutes the remaining pieces of tumor were inserted into the pocket. After that, the incision was closed.

The patient was awake and fully oriented throughout the procedure. The patient continued a course of Augmentin for antibiotic prophylaxis.

Surveillance scans two to four weeks after the second implant demonstrated progression of the disease process. A Left upper lobe lung lesion has enlarged to 1.5 cm. A new right chest wall mass has eroded into the posterior 7$^{th}$ rib causing a pathological fracture. Her Left pelvic mass has increased in size to 5.5 cm and a new right iliac bone metastasis was identified.

The Third Chimeric Tumor Autoimplant

Sixty-one days after the first tumor implant, the patient underwent placement of fiducial markers, by interventional radiology into her right chest wall lesion in preparation for cyberknife radiation later. At the time of this procedure, the tumor was also injected with the DTaP vaccine, Adacel. The following day she experienced rigors and fevers up to 103.7. These were managed with Motrin and subsided to intermittent low-grade fevers no higher than 99.4.

On that day the patient also received her sixth dose of Opdivo and Yervoy, both at 3 mg/kg. Her laboratory values were within normal limits. She tolerated her infusions well.

For the third autoimplantation of the chimeric PDX tumor as a booster, in addition to using PDZ, tumor pieces, a mixed vaccine inculum using a standard DTaP vaccine mixed with isolated killed tumor cells taken from the patient with the objective of inciting an anti-tumor immune response under cover of her dual checkpoint inhibitors.

For the third implantation, PDX tumor, AJR-S3, was frozen in sterile Saline with Levofloxacin at −80 degrees Celsius to achieve cryo-killing of the tumor. The day after the patient received her sixth dose of Nivolumab/Ipilimumab, the AJR-53 tumor was irradiated with 4000 rads of gamma-radiation to inactivate any living cancer cells and thawed.

Prior to the procedure, the patient started a prophylactic course of Augmentin. She also treated herself, prophylactically, with Benadryl, Zyrtec, Percocet and Ibuprofen immediately prior to autoimplantation.

Pre-operative laboratory studies on revealed no abnormalities. She demonstrated a continued Eosinophilia, a likely side effect of her Yervoy (ipilimumab) therapy.

The AJR-S3 PDX tumor pieces were minced up into small pieces under sterile condition and placed in a sterile tray containing saline with ciprofloxacin on the sterile field.

After she gave informed consent, the patient positioned herself in a left right lateral decubitus position, with right side up. The operative area was prepared with chlorohexidine and blocked using 20 cc of a standard 1% lidocaine with epinephrine solution. The epidermis and dermis were blocked with 10 cc 1% lidocaine without epinephrine in light of dermal necrosis seen after the second implant. The patient was injected 20 cc Lidocaine with Epinephrine deep in the area of the planned subcutaneous pocket. After ensuring achievement of total analgesia, a ¾ inch incision was made on the patient's right lateral mid-thigh region postero-inferior to a prior PDX implantation site (i.e., first implant) to create a subcutaneous pocket.

Minced PDX tumor bits (a total of 3 crn 2) was inserted into the subcutaneous pocket and delivered to the base of the pocket. After ten minutes the incision was closed. The patient was stable and communicating throughout the procedure.

Two 1 cc single cell tumor cell preps obtained from the metastatic lesion resected from the patient's right upper lung lobe prior to commencement of treatment with Nivolumab and Ipilimumab, AR-V1 and AR-V2, cryo killed at −80 and irradiated with 4000 rads of gamma radiation were used in the mixed vaccine inculum noted above. This 2 cc cryo-killed cell prep was then mixed vigorously with the Boosterix DTaP vaccine using a two-way connector to ensure vaccine homogeneity. This preparation was then injected into The patient's left thigh inferior to a prior implant site (i.e., the second implant).

The patient was awake and fully oriented throughout the procedure. The patient continued a course of Augmentin for antibiotic prophylaxis.

The Fourth Chimeric Tumor Autoimplant

For the fourth autoimplantation of the chimeric PDX tumor as a booster PDX tumor, preparations AJR-S7 and AJR-S-8 were used. PDX tumor, AJR-S7, was frozen in sterile Saline with Ciprofloxacin at −80 degrees Celsius to achieve cryo-killing of the tumor. The PDX tumor prep labeled AJR-58 was fresh harvested on the day of the implantation. On the same day that AJR-S8 was harvested both the AJR-S7 and AJR-S8 PDX tumor preparations were irradiated with approximately 3500 rads of gamma-radiation to inactivate any living cancer cells.

Prior to the procedure, the patient started a prophylactic course of Augmentin. She also treated herself, prophylactically, with Benadryl, Oxycodone, and Zyrtec immediately prior to autoimplantation. She had also taken prednisone.

The AJR-S7 and S8 PDX tumor pieces were minced up into small pieces under sterile condition and placed in a sterile tray containing saline with ciprofloxacin on the sterile field.

After she gave informed consent, the patient positioned herself in a left lateral decubitus position, with right side up. The operative area was prepared with betadine and blocked using 3 cc of a standard 2% Lidocaine The epidermis and dermis were blocked with 10 cc 1% Lidocaine. After ensuring achievement of total analgesia, a ¾ inch incision was made on the patient's right lateral thigh to create a subcutaneous pocket.

Minced tumor bits (a total of 4 cm$^2$) were inserted into the subcutaneous pocket and delivered to the base of the pocket. After ten minutes the incision was closed. The patient was awake and fully oriented throughout the procedure.

The Fifth Chimeric Tumor Autoimplant

Figure 6:
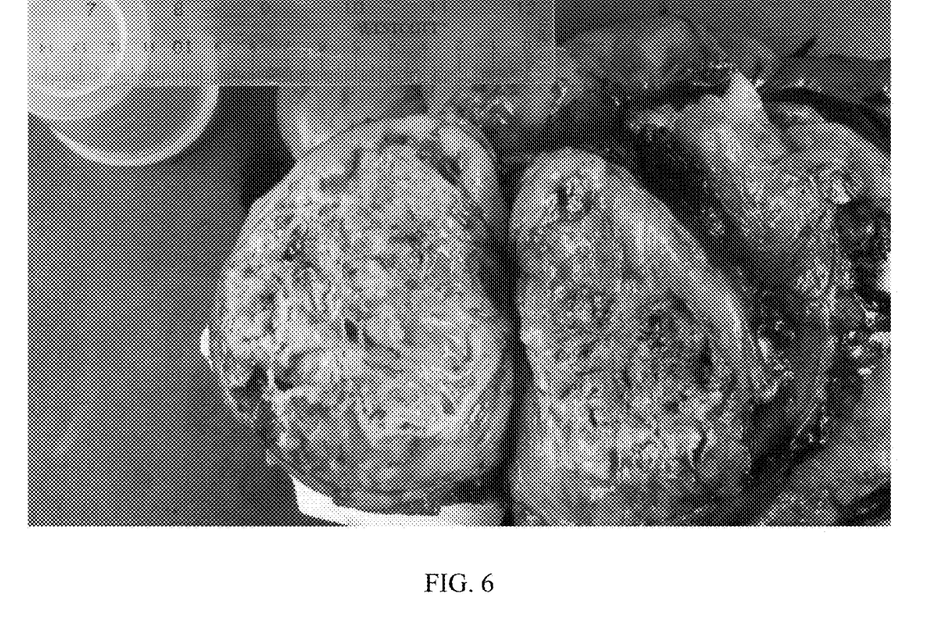
FIG. 6 shows a large necrotic tumor in the index patient following four rounds of PDX autoimplantation with the PDX tumor.
Figure 7:
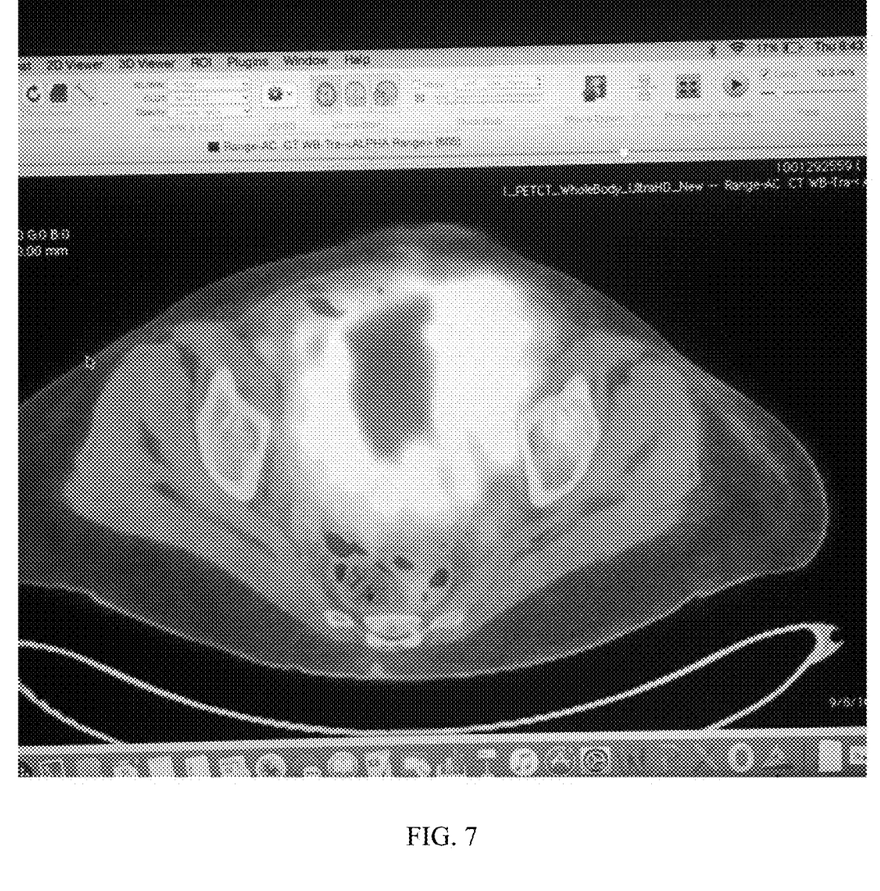
FIG. 7 is a PET scan of a tumor removed from the index patient after four implants of DX material according to the present invention demonstrating extremely avid FDG uptake consistent with ongoing inflammation with significant areas of tumor necrosis.

Following the fourth chimeric tumor implant, PET scan and histological findings indicated an immune response as shown in FIGS. 6 and 7, but the Leiomyosarcoma continued to advance and resections of a mass in the patient's pelvis and on lesion on her spine were carried out as well as cryoablation of left and right lung lesions and a hepatic lesion. After surgical excision, the tumor shown in FIGS. 6 and 7 was examined and gross pathology demonstrated over 70% necrosis as seen in FIG. 7. The resected tumor exhibited marked evidence of reversion to a PDL-1 positive phenotype which is consistent with active inflammation. The patient's tumors following initiation of immunotherapy demonstrated evidence of diffuse infiltration with CD4 positive T-lymphocytes.

Subsequently the patient commenced a course of metronomic cyclophosphamide and propranolol and re-initiated letrozole therapy.

Tumor parts taken from the tumor shown in FIGS. 6 and 7 during resection of her pelvic mass were implanted into recipient NSG mice to generate PDX mice, as described above.

The fifth chimeric tumor autoimplant was carried out three hundred and fifty-five days after the first implant and one hundred and twenty-two days after resection of the pelvic mass and implantation of tumor portions into mice.

The day prior to the implantation AJR-S10 and AJR-S12 PDX tumor samples were harvested from the mice frozen in sterile saline with ciprofloxacin at −80° C. to cryo-kill the tumor and irradiated with approximately 2000 rads of gamma radiation to inactivate any living cancer cells.

Prior to the procedure, the patient started a prophylactic course of Augmentin. She also treated herself, prophylactically, with Benadryl, Oxycodone, and Zyrtec immediately prior to autoimplantation.

The AJR-S10 and S12 PDX tumor pieces were minced up into small pieces under sterile condition and placed in a sterile tray containing saline with ciprofloxacin on the sterile field. A single dose of the vaccine StroVac was added to the preparation with the objective of inducing a robust inflammatory response at the PDX-tumor implant site.

After she gave informed consent, the patient positioned herself in a left lateral decubitus position, with right side up. The operative area was prepared with betadine and the dermis and epidermis blocked using 20 cc 1% Lidocaine, After ensuring achievement of total analgesia, a 1 inch incision was made on the patient's right lateral thigh to create a subcutaneous pocket.

Minced PDX tumor bits (a total of 5-6 cm$^3$) was inserted into the subcutaneous pocket and delivered to the base of the pocket. After ten minutes the incision was closed. The patient was awake and fully oriented throughout the procedure.

Figure 8:
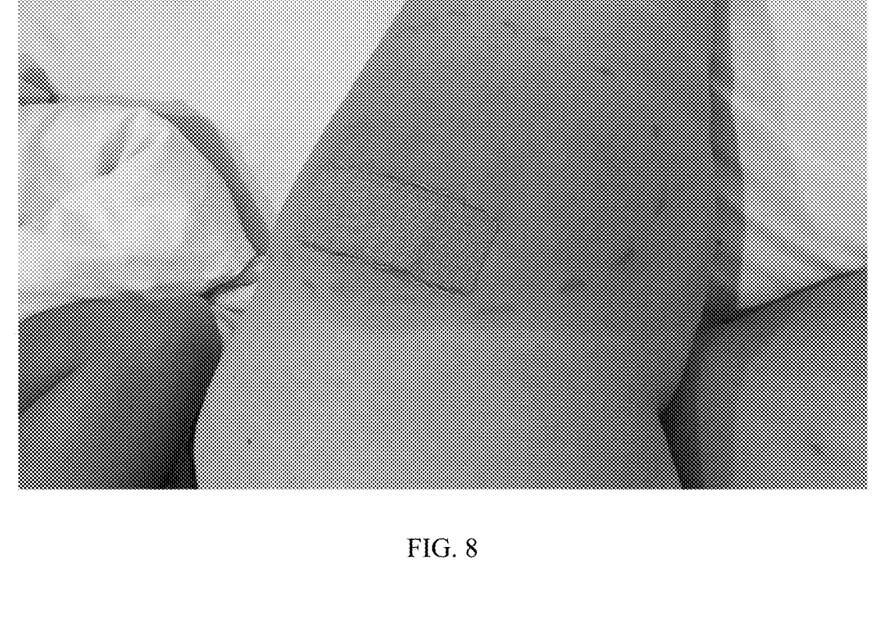
FIG. 8 shows inflammatory response in the area of implantation in a patient's thigh.

Overall, following every implant the index patient experienced an impressive local inflammatory response, as shown in representative FIGURE X (PLEASE ADD FIG. 8). This inflammatory response occurred concomitantly with regional inguinal lymphadenopathy consistent with an ongoing immune response. Additionally, the local inflammatory response in the thighs was visible and lasted from 2-7 days.

The invention claimed is:

1. A method for treating a human or other animal patient having cancerous tumors which comprises:
   1) Removing at least part of a tumor from the patient;
   2) Implanting the tumor in an immunodeficient recipient host animal;
   3) Allowing the tumor to grow in said recipient host animal to form a host animal/patient chimeric tumor;
   4) Removing at least part of the chimeric tumor from the host animal;
   5) Destroying or attenuating live chimeric tumor cells in said removed part of the chimeric tumor; and
   6) Implanting into the original donor patient all or part of said removed part of said chimeric tumor in which live chimeric tumor cells have been destroyed or attenuated.

2. The method as claimed in claim 1, wherein said tumor is selected from the group consisting of sarcoma, adenocarcinoma, melanoma, and other solid tumors.

3. The method as claimed in claim 1, wherein the tumor has metastasized.

4. The method as claimed in claim 1, wherein the immunodeficient host animal is selected from the group consisting of immunodeficient mice, immunodeficient rats and immunodeficient pigs.

5. The method as claimed in claim 1, wherein said immunodeficient host animal is a NOD/scid mouse, a nude mouse or a transgenic modification thereof.

6. The method as claimed in claim 1, wherein the tumor or tumor part removed from the patient is implanted subcutaneously in the host immunodeficient animal.

7. The method as claimed in claim 1, wherein the tumor implanted in the host animal is allowed to grow for from 2 to 6 months before removal for implanting into the donor patient.

8. The method as claimed in claim 1, wherein said implanted tumor is injected with one or more immunostimulatory TLR agonists.

9. The method as claimed in claim 8, wherein the TLR agonist is a TLR-9 agonist.

10. The method as claimed in claim 1, wherein prior to removal of the chimeric tumor from the host immunodeficient animal, its chimeric nature is confirmed by immunohistochemistry or molecular assays.

11. The method as claimed in claim 1, wherein after removal from the host immunodeficient animal, the chimeric tumor or part thereof that is to be implanted into the patient is treated to destroy or attenuate live cancer cells by irradiation.

12. The method as claimed in claim 1, wherein after removal from the host immunodeficient animal, the chimeric tumor or part thereof that is to be implanted into the patient is treated to destroy live cancer cells by cryo-killing.

13. The method as claimed in claim 1, wherein after removal from the host immunodeficient animal, the chimeric tumor or part thereof that is to be implanted into the patient is stored by freezing sterile saline and held at a temperature below −80° C. followed by repeated freeze-thaw cycles.

14. The method as claimed in claim 1, wherein, the chimeric tumor or part thereof that is to be implanted into the patient is implanted, in live form, after removal from the host immunodeficient animal.

15. The method as claimed in claim 1, wherein after removal from the host immunodeficient animal, the chimeric tumor or part thereof is implanted into a subcutaneous pocket in the arms, thighs or flank of the patient.

16. The method as claimed in claim 1, wherein the chimeric tumor or part thereof is implanted into the patient in the form of pieces of a size of from 1-3.5 cm³.

17. The method as claimed in claim 1, wherein the chimeric tumor or part thereof that is implanted into the patient is minced prior to implantation.

18. The method of claim 1, wherein said implantation locates at least part of said chimeric tumor adjacent a plane in the patient's subcutaneous fat.

19. The method as claimed in claim 1, wherein said implantation of material from said chimeric tumor is repeated multiple times over a period of three to eight weeks.

20. The method of claim 1, further comprising treating the subject with a checkpoint inhibitor.

21. The method of claim 1, further comprising administering to the subject an adjunctive therapy that renders other indigenous metastatic lesions of the donor patient susceptible to immunological attack said therapy being selected from the group consisting of direct intra-tumoral injection with microbial derivatives, synthetic immunogenic biologics, cryoablation, stereotactic radiation and combinations thereof.

* * * * *